US00PP24423P3

(12) United States Plant Patent
Groves

(10) Patent No.: US PP24,423 P3
(45) Date of Patent: May 6, 2014

(54) ***ROSMARINUS* PLANT NAMED 'SUNKISSED'**

(50) Latin Name: *Rosmarinus officinalis*
Varietal Denomination: Sunkissed

(75) Inventor: Elliot Groves, New Plymouth (NZ)

(73) Assignee: Lowaters Nursery, Southampton, Hampshire (GB)

( * ) Notice: Subject to any disclaimer, the term of this patent is extended or adjusted under 35 U.S.C. 154(b) by 70 days.

(21) Appl. No.: 13/507,489

(22) Filed: Jul. 3, 2012

(65) Prior Publication Data

US 2013/0014301 P1 Jan. 10, 2013

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — C. A. Whealy

(57) ABSTRACT

A new and distinct cultivar of *Rosmarinus* plant named 'Sunkissed', characterized by its upright and somewhat outwardly spreading plant habit; green and golden yellow bi-colored leaves; blue-colored flowers and good garden performance.

1 Drawing Sheet

Botanical designation: *Rosmarinus officinalis*.
Cultivar denomination: 'SUNKISSED'.

BACKGROUND OF THE INVENTION

The present invention relates to a new and distinct cultivar of *Rosmarinus* plant, botanically known as *Rosmarinus officinalis,* commercially known as Rosemary and hereinafter referred to by the name 'Sunkissed'.

The new *Rosmarinus* plant is a naturally-occurring whole plant mutation of an unnamed selection of *Rosmarinus officinalis,* not patented. The new *Rosmarinus* plant was discovered and selected by the Inventor in December, 2007 from within a population of plants of the parent selection in a controlled greenhouse environment in New Plymouth, New Zealand.

Asexual reproduction of the new *Rosmarinus* plant by terminal cuttings in a controlled greenhouse environment in New Plymouth, New Zealand since the spring of 2008 has shown that the unique features of this new *Rosmarinus* plant are stable and reproduced true to type in successive generations.

SUMMARY OF THE INVENTION

Plants of the new *Rosmarinus* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sunkissed'. These characteristics in combination distinguish 'Sunkissed' as a new and distinct *Rosmarinus* plant:

1. Upright and somewhat outwardly spreading plant habit.
2. Green and golden yellow bi-colored leaves.
3. Blue-colored flowers.
4. Good garden performance.

Plants of the new *Rosmarinus* differ from plants of the mutation parent selection primarily in leaf color as plants of the mutation parent selection have solid green-colored leaves.

Plants of the new *Rosmarinus* can be compared to plants of *Rosmarinus officinalis* 'Gold Dust', disclosed in U.S. Plant Pat. No. 19,949. Plants of the new *Rosmarinus* and 'Gold Dust' differ primarily in plant habit as plants of the new *Rosmarinus* are more uniform than plants of 'Gold Dust'.

BRIEF DESCRIPTION OF THE PHOTOGRAPHS

The accompanying photographs illustrate the overall appearance of the new *Rosmarinus* plant showing the colors as true as it is reasonably possible to obtain in colored reproductions of this type. Colors in the photographs may differ slightly from the color values cited in the detailed botanical description which accurately describe the colors of the new *Rosmarinus* plant.

The photograph at the bottom of the sheet comprises a side perspective view of a typical flowering plant of 'Sunkissed' grown in a container.

The photograph at the top of the sheet is a close-up view of a typical flowering plant of 'Sunkissed'.

DETAILED BOTANICAL DESCRIPTION

The aforementioned photographs, following observations and measurements describe plants grown during the summer in 15.24-cm containers in an outdoor nursery in Fresno, Calif. and under cultural practices which approximate those generally used in commercial *Rosmarinus* production. Plants were twelve weeks old when the photographs and description were taken. During the production of the plants, day temperatures ranged from 15° C. to 27° C. and night temperatures ranged from 3° C. to 15° C. In the following description, color references are made to The Royal Horticultural Society Colour Chart, 2007 Edition, except where general terms of ordinary dictionary significance are used.

Botanical classification: *Rosmarinus officinalis* 'Sunkissed'.

Parentage: Naturally-occurring whole plant mutation of an unnamed selection of *Rosmarinus officinalis,* not patented.

Propagation:

*Type.*—Vegetative cuttings.

*Time to initiate roots, summer.*—About five weeks at 21° C.

*Time to produce a rooted young plant, summer.*—About two months at 18° C.

*Root description.*—Fibrous.

Plant description:

*Plant and growth habit.*—Herbaceous perennial sub-shrub; upright and somewhat outwardly spreading plant habit; moderately vigorous growth habit; freely branching habit, pinching enhances lateral branch development, dense and bushy plant form.

*Plant height.*—About 30 cm.

*Plant width* (*spread*).—About 30 cm to 35 cm.

*Lateral branch description.*—Length: About 14 cm to 18 cm. Diameter: About 2 mm. Internode length: About 1.5 cm to 2 cm. Strength: Strong. Aspect: Upright to somewhat outwardly spreading. Texture: Smooth, glabrous. Color, immature: Close to 144B. Color, mature: Close to N199B.

*Foliage description.*—Arrangement: Opposite, simple; sessile. Length: About 2.8 cm to 3.5 cm. Width: About 4 mm. Shape: Lanceolate. Apex: Acute. Base: Cuneate. Margin: Entire, revolute. Texture, upper and lower surfaces: Pubescent. Fragrance: Aromatic, pungent. Venation pattern: Pinnate. Color: Developing leaves, upper surface: Between N138C and 191A. Developing leaves, lower surface: Close to N138C. Fully expanded leaves, upper surface: Close to 189A; venation, close to 189A. Fully expanded leaves, lower surface: Close to 191A; venation, close to 191B.

Flower description:

*Flower arrangement and shape.*—Single sessile flowers arranged in compact verticillasters on crowded spikes; freely flowering habit; flowers tubular with a two-lobed upper lip and a three-lobed lower lip and relatively long showy terminal flower bracts.

*Natural flowering season.*—Long flowering period; flowering continuous from the spring through the summer in Denmark.

*Flower longevity on the plant.*—Longevity of individual flowers is highly dependent on weather conditions; flowers not persistent; terminal flower bracts persistent.

*Fragrance.*—None detected.

*Flower buds.*—Length: About 7 mm. Diameter: About 2 mm. Shape: Oblong. Color: Close to N92C.

*Inflorescence size.*—Height: About 3 cm to 4 cm. Diameter: About 1.5 cm.

*Flowers.*—Diameter: About 1 cm. Depth (height): About 6 mm.

*Petals.*—Length: About 2 mm. Width: About 1 mm to 2 mm. Shape: Roughly spatulate to oval. Apex: Rounded. Margin: Entire. Texture, upper and lower surfaces: Smooth, glabrous. Color: When opening and fully opened, upper surface: Close to N92C; tube, white. When opening and fully opened, lower surface: Close to N92C; tube, white.

*Sepals.*—Arrangement: Five sepals fused into a tube. Length: About 8 mm. Width: About 2 mm. Shape: Lanceolate. Apex: Four have acute apices; the apex of the fifth sepal is rounded to cordate. Margin: Entire. Texture, upper and lower surfaces: Tomentose, wooly. Color, upper and lower surfaces: Close to 143B; towards the base, lighter than 143B.

*Peduncles.*—Length: About 6 cm to 6.5 cm. Diameter: About 2 mm. Strength: Strong. Aspect: Mostly upright. Color: Close to 143B.

*Reproductive organs.*—Stamens: Quantity per flower: Four. Anther shape: Reniform. Anther length: About 0.5 mm. Pollen amount: Scarce. Pollen color: Yellow orange. Pistils: Quantity per flower: One. Pistil length: About 5 mm. Stigma shape: Club-shaped. Stigma color: Dark purple. Style length: About 4 mm. Style color: Whitish. Ovary color: Yellow green.

*Seeds.*—Length: About 3 mm. Diameter: About 2 mm.

Disease & pest resistance: Plants of the new *Rosmarinus* have not been noted to be resistant to pathogens and pests common to *Rosmarinus* plants.

Garden performance: Plants of the new *Rosmarinus* have exhibited good garden performance and to have good tolerance to rain and wind.

It is claimed:

1. A new and distinct *Rosmarinus* plant named 'Sunkissed' as illustrated and described.

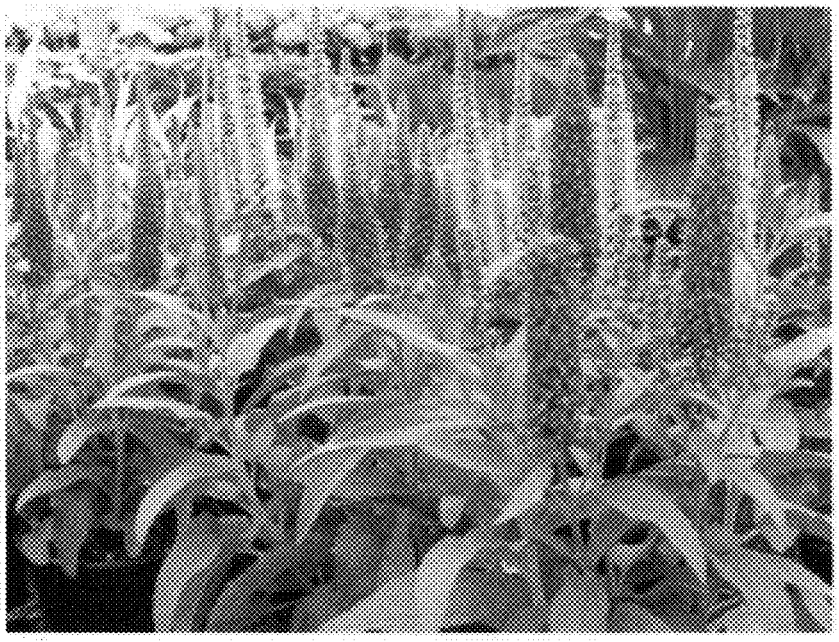
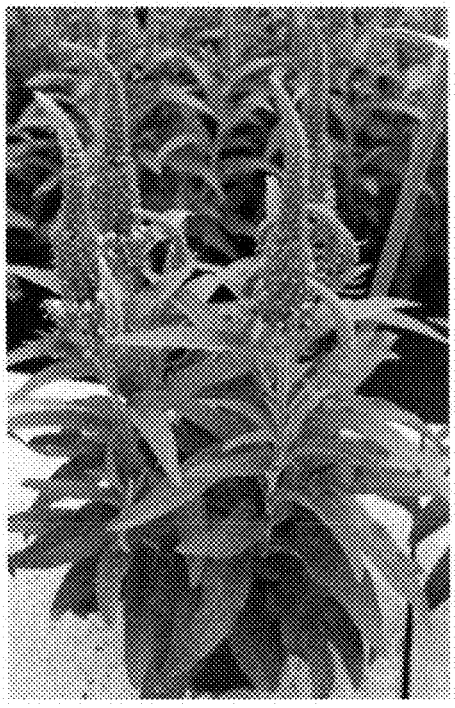

* * * * *